United States Patent
Wawro et al.

(10) Patent No.: US 11,251,635 B2
(45) Date of Patent: Feb. 15, 2022

(54) VITAL SIGNS MONITOR WITH A REMOVABLE AND DISCHARGABLE BATTERY

(71) Applicant: Welch Allyn, Inc., Skaneateles Falls, NY (US)

(72) Inventors: Thaddeus J. Wawro, Auburn, NY (US); David M. Antos, Constantia, NY (US); Jennifer Bergstrom, Portland, OR (US); Kenneth V Coon, III, Jordan, NY (US); Jennifer M. Grant, Syracuse, NY (US); Scott A. Martin, Camillus, NY (US); Carlos A. Suarez, Syracuse, NY (US)

(73) Assignee: Welch Allyn, Inc., Skanesteles Falls, NY (US)

( * ) Notice: Subject to any disclaimer, the term of this patent is extended or adjusted under 35 U.S.C. 154(b) by 565 days.

(21) Appl. No.: 15/993,667

(22) Filed: May 31, 2018

(65) Prior Publication Data
US 2019/0190293 A1 Jun. 20, 2019

Related U.S. Application Data

(60) Provisional application No. 62/640,146, filed on Mar. 8, 2018, provisional application No. 62/607,646, filed on Dec. 19, 2017.

(51) Int. Cl.
*H02J 7/00* (2006.01)
*A61B 5/00* (2006.01)
(Continued)

(52) U.S. Cl.
CPC ............ *H02J 7/0063* (2013.01); *A61B 5/259* (2021.01); *A61B 5/6832* (2013.01);
(Continued)

(58) Field of Classification Search
CPC .................. H02J 7/0063; H02J 7/0042; H02J 2007/0067; A61B 5/04087; A61B 5/6832;
(Continued)

(56) References Cited

U.S. PATENT DOCUMENTS

| 3,784,460 A | 1/1974 | Le Bras et al. |
| 4,128,173 A | 12/1978 | Lazarus et al. |

(Continued)

FOREIGN PATENT DOCUMENTS

| CN | 2496394 Y | 6/2002 |
| CN | 101167648 A | 4/2008 |

(Continued)

OTHER PUBLICATIONS

European Search Report for EP Application 18212458.6; dated May 15, 2019; Place of search—The Hague; Date of completion of the search—May 9, 2019.

*Primary Examiner* — Linda C Dvorak
*Assistant Examiner* — Nils A Potter
(74) *Attorney, Agent, or Firm* — Lee & Hayes, P.C.

(57) ABSTRACT

A vital signs monitor includes an equipment housing defining an equipment compartment, a circuit assembly and a battery residing inside the equipment compartment, an electrical connector forming a connection between the battery assembly and the circuit assembly, and a battery discharge circuit. A retainer joined to the equipment housing retains the battery assembly in the housing. The retainer is separable from the housing so that its separation causes a break in the electrical connection and activates the discharge circuit.

20 Claims, 8 Drawing Sheets

(51) Int. Cl.
*A61N 1/36* (2006.01)
*A61N 1/375* (2006.01)
*A61B 5/259* (2021.01)
*A61B 5/0245* (2006.01)

(52) U.S. Cl.
CPC .......... *A61N 1/3603* (2017.08); *A61N 1/375* (2013.01); *H02J 7/0042* (2013.01); *A61B 5/0245* (2013.01); *A61B 2560/0204* (2013.01); *A61B 2560/045* (2013.01); *A61B 2560/0412* (2013.01); *A61B 2560/0468* (2013.01); *A61B 2562/164* (2013.01); *A61B 2562/166* (2013.01); *H02J 2007/0067* (2013.01)

(58) Field of Classification Search
CPC .... A61B 2560/0412; A61B 2560/0204; A61B 2562/164; A61B 2560/0468; A61B 2562/166; A61B 2560/045; A61B 5/0245; A61B 5/0402; A61N 1/3603; A61N 1/375; H01M 2/1022
USPC ........................................................ 600/372
See application file for complete search history.

(56) References Cited

U.S. PATENT DOCUMENTS

| | | | |
|---|---|---|---|
| 4,314,554 A | 2/1982 | Greatbatch | |
| 4,408,263 A | 10/1983 | Sternlicht | |
| 4,522,302 A | 6/1985 | Paikoff | |
| 5,306,235 A | 4/1994 | Haynes | |
| 5,445,608 A | 8/1995 | Chen et al. | |
| 5,634,921 A | 6/1997 | Hood et al. | |
| 5,697,896 A | 12/1997 | McNichols et al. | |
| 5,697,946 A | 12/1997 | Hopper et al. | |
| 5,851,221 A | 12/1998 | Rieder et al. | |
| 5,868,794 A * | 2/1999 | Barkley | A61N 1/3931 607/5 |
| 5,885,211 A | 3/1999 | Eppstein et al. | |
| 5,978,701 A | 11/1999 | Johnson et al. | |
| 5,983,130 A | 11/1999 | Phipps et al. | |
| 6,035,234 A | 3/2000 | Riddle et al. | |
| 6,086,572 A | 7/2000 | Johnson et al. | |
| 6,136,839 A | 10/2000 | Isakson et al. | |
| 6,148,232 A | 11/2000 | Avrahami | |
| 6,162,214 A | 12/2000 | Mueller et al. | |
| 6,210,425 B1 | 4/2001 | Chen | |
| 6,238,338 B1 * | 5/2001 | DeLuca | A61B 5/0024 600/300 |
| 6,273,904 B1 | 8/2001 | Chen et al. | |
| 6,350,772 B1 | 2/2002 | Kuroiwa et al. | |
| 6,416,531 B2 | 7/2002 | Chen | |
| 6,445,011 B1 | 9/2002 | Hirano et al. | |
| 6,454,789 B1 | 9/2002 | Chen et al. | |
| 6,591,124 B2 | 7/2003 | Sherman et al. | |
| 6,602,274 B1 | 8/2003 | Chen | |
| 6,611,706 B2 | 8/2003 | Avrahami et al. | |
| 6,661,167 B2 | 12/2003 | Eliashevich et al. | |
| 6,662,044 B2 | 12/2003 | Crawford et al. | |
| 6,689,380 B1 | 2/2004 | Marchitto et al. | |
| 6,748,266 B2 | 6/2004 | Bemabei | |
| 7,010,343 B2 | 3/2006 | Bemabei | |
| 7,141,034 B2 | 11/2006 | Eppstein et al. | |
| 7,208,119 B1 * | 4/2007 | Kurtock | A61B 5/14532 422/430 |
| 7,392,080 B2 | 6/2008 | Eppstein et al. | |
| 7,537,590 B2 | 5/2009 | Santini, Jr. et al. | |
| 7,853,320 B1 | 12/2010 | Sexton | |
| 8,057,464 B2 | 11/2011 | Chen et al. | |
| 8,095,213 B1 | 1/2012 | Sexton | |
| 8,214,031 B1 | 7/2012 | Sexton | |
| 2004/0204673 A1 | 10/2004 | Flaherty | |
| 2008/0208107 A1 | 8/2008 | McRae et al. | |
| 2010/0063438 A1 * | 3/2010 | Bengtsson | A61M 5/14248 604/66 |
| 2015/0050532 A1 * | 2/2015 | Waigel | B25F 5/008 429/61 |
| 2016/0120411 A1 | 5/2016 | Hadley et al. | |
| 2016/0183854 A1 | 6/2016 | Lee | |
| 2016/0249915 A1 * | 9/2016 | Beckman | H02J 7/0045 227/175.1 |
| 2017/0086826 A1 * | 3/2017 | Leimbach | H01M 10/44 |
| 2017/0072217 A1 | 6/2017 | Klem et al. | |
| 2017/0215776 A1 * | 8/2017 | Frey | A61B 5/6833 |
| 2017/0246063 A1 | 8/2017 | Monson et al. | |
| 2017/0353046 A1 * | 12/2017 | Chen | H02J 7/0044 |
| 2018/0021184 A1 | 1/2018 | Monson et al. | |
| 2018/0078163 A1 * | 3/2018 | Welch | A61B 5/01 |
| 2020/0029902 A1 * | 1/2020 | Kube | A61B 5/6833 |

FOREIGN PATENT DOCUMENTS

| | | |
|---|---|---|
| CN | 206443688 U | 8/2017 |
| EP | 2422693 | 2/2012 |
| EP | 2422693 A1 | 2/2012 |
| WO | 2015127218 A1 | 8/2015 |
| WO | 2017058591 A1 | 4/2017 |

\* cited by examiner

VITAL SIGNS MONITOR WITH A REMOVABLE AND DISCHARGABLE BATTERY

CROSS-REFERENCE TO RELATED PATENT APPLICATIONS

This application claims priority to U.S. Provisional Applications 62/607,646 filed on Dec. 19, 2017 and 62/640,146 filed on Mar. 8, 2018, the contents of both of which are incorporated herein by reference.

TECHNICAL FIELD

The subject matter described herein relates to medical vital signs monitors and particularly to a battery powered disposable monitor whose battery is removable prior to disposal of the monitor and in which removal of the battery activates a battery discharge circuit.

BACKGROUND

Wearable monitors for monitoring the vital signs of a subject, such as a hospital patient, may be designed for use by a single patient for a limited time, for example for about five days. An on-board battery may be provided to supply electrical energy to the electrical components of the monitor. However environmental regulations may prohibit the disposal of batteries as hospital waste. As a result, when the time arrives to dispose of the monitor it is necessary to first remove the battery from the monitor. Moreover it may also be necessary to discharge the battery.

The vital signs monitor described herein includes a removable battery and is adapted to discharge the battery at the time of removal. The monitor includes an ON/OFF switch, a battery, a circuit assembly, and a battery discharge circuit. The monitor is adapted to not discharge the battery in response to an interruption of electrical communication between the battery and the circuit assembly by way of the switch and to discharge the battery in response to interruption of the electrical communication between the battery and the circuit assembly by an action other than use of the switch.

SUMMARY

One embodiment of a vital signs monitor described herein includes an equipment housing defining an equipment compartment, a circuit assembly and a battery residing inside the equipment compartment, an electrical connector forming a connection between the battery assembly and the circuit assembly, and a battery discharge circuit. A retainer joined to the equipment housing retains the battery assembly in the housing. The retainer is separable from the housing so that its separation causes a break in the electrical connection and activates the discharge circuit.

BRIEF DESCRIPTION OF THE DRAWINGS

The foregoing and other features of the various embodiments of the vital signs monitor described herein will become more apparent from the following detailed description and the accompanying drawings in which.

Features similar to or the same as features already described may be identified herein by the same reference numerals already used.

DESCRIPTION

The contents of U.S. Provisional Applications 62/588,598 entitled "Modular Vital Signs Monitor", filed on Nov. 20, 2017 and 62/592,602 entitled "Modular Vital Signs Monitor", filed on Nov. 30, 2017 are expressly incorporated herein by reference. The removable and dischargable battery embodiments described herein may be used in conjunction with various vital signs monitor architectures including those described in the '598 and '602 applications.

Figure 1:
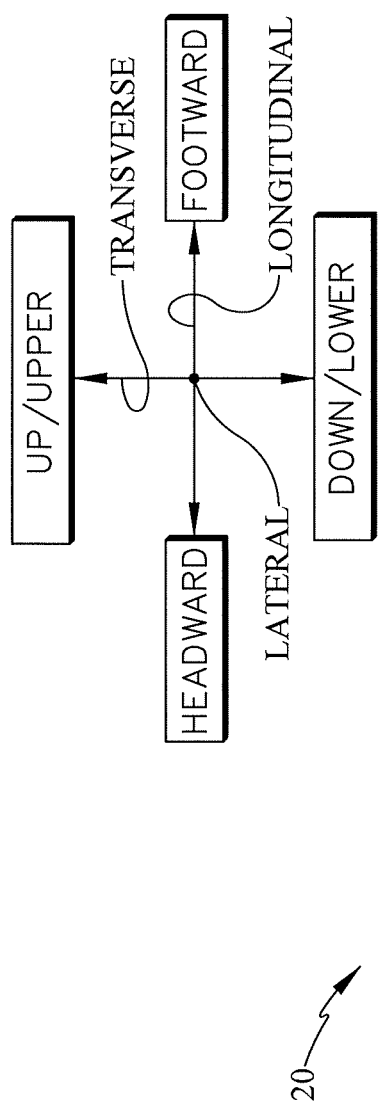
FIG. 1 is a cross sectioned elevation view of a vital signs monitor including a pair of cleats, an equipment module having a housing, a battery assembly residing inside the equipment module, and a battery retainer.
Figure 1:
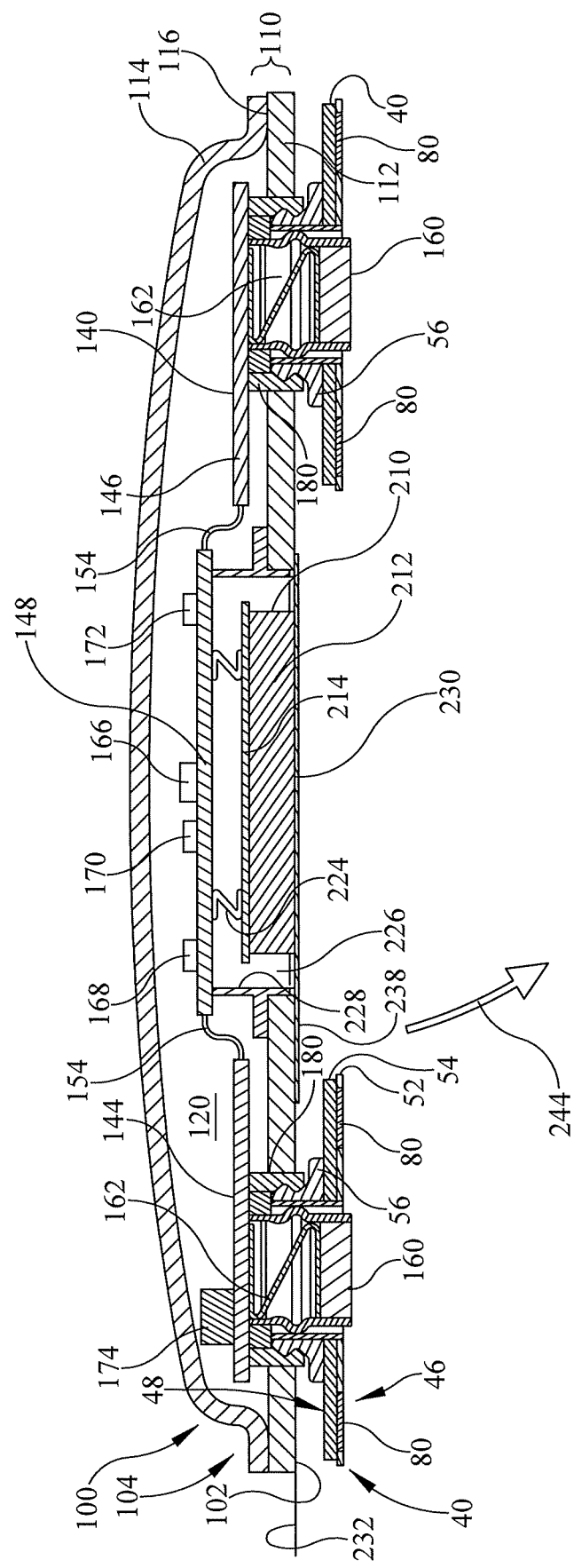
Figure 2:
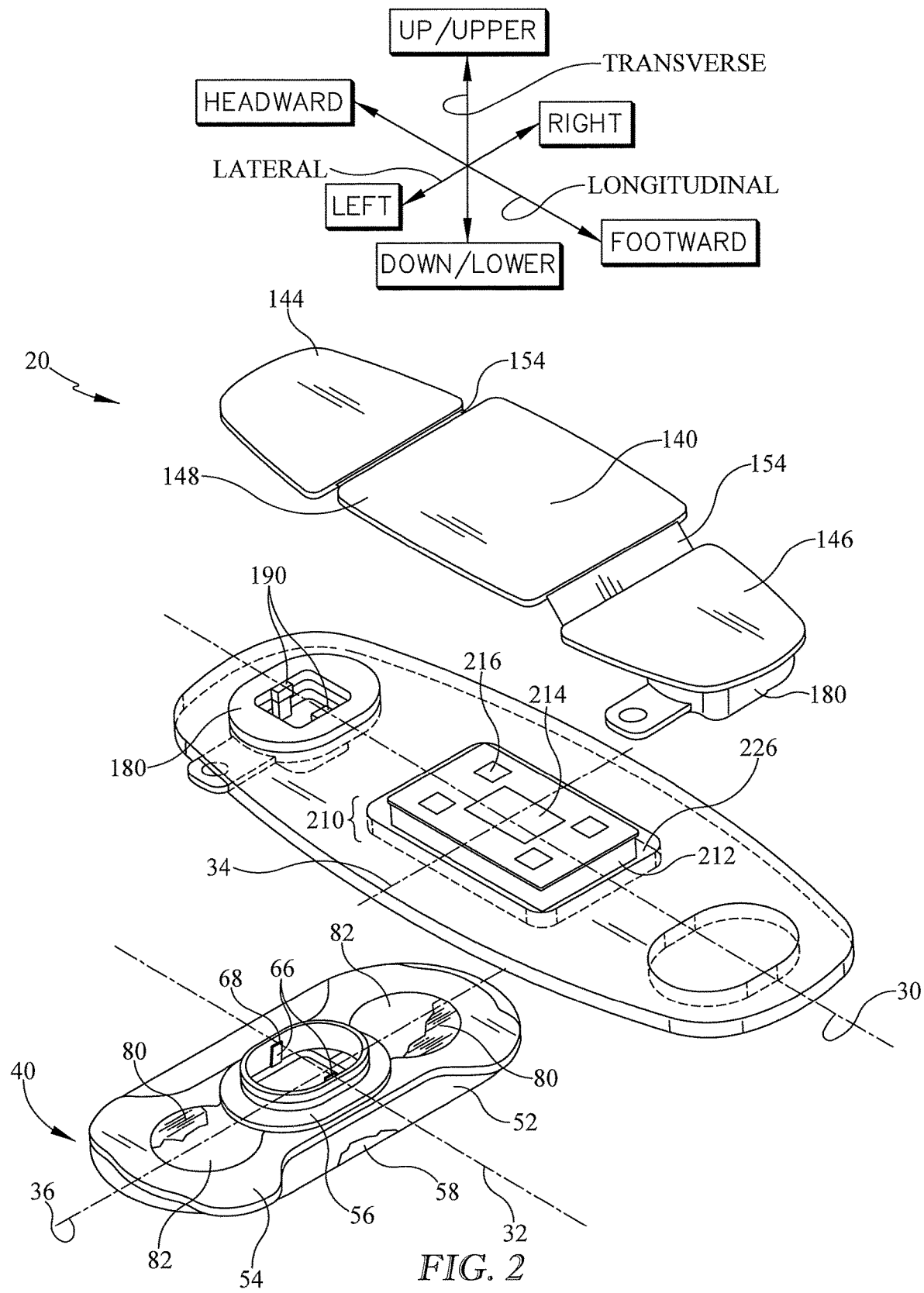
FIG. 2 is an exploded perspective view of selected elements of the monitor of FIG. 1.

FIGS. 1-2 show a vital signs monitor 20 which is wearable by a subject such as a hospital patient. FIGS. 1 and 2 also include mutually orthogonal longitudinal, lateral, and transverse reference axes. As indicated by the labels on the axes, directional distinctions are indicated by "headward" and "footward" in the longitudinal direction, "left" and "right" in the lateral direction, and "up" and "down" or "upper" and "lower" in the transverse direction. FIG. 2 also shows longitudinally extending centerlines 30, 32 of housing and cleat components of the monitor as well as laterally extending centerlines 34, 36 of the housing and cleat components.

Figure 3:
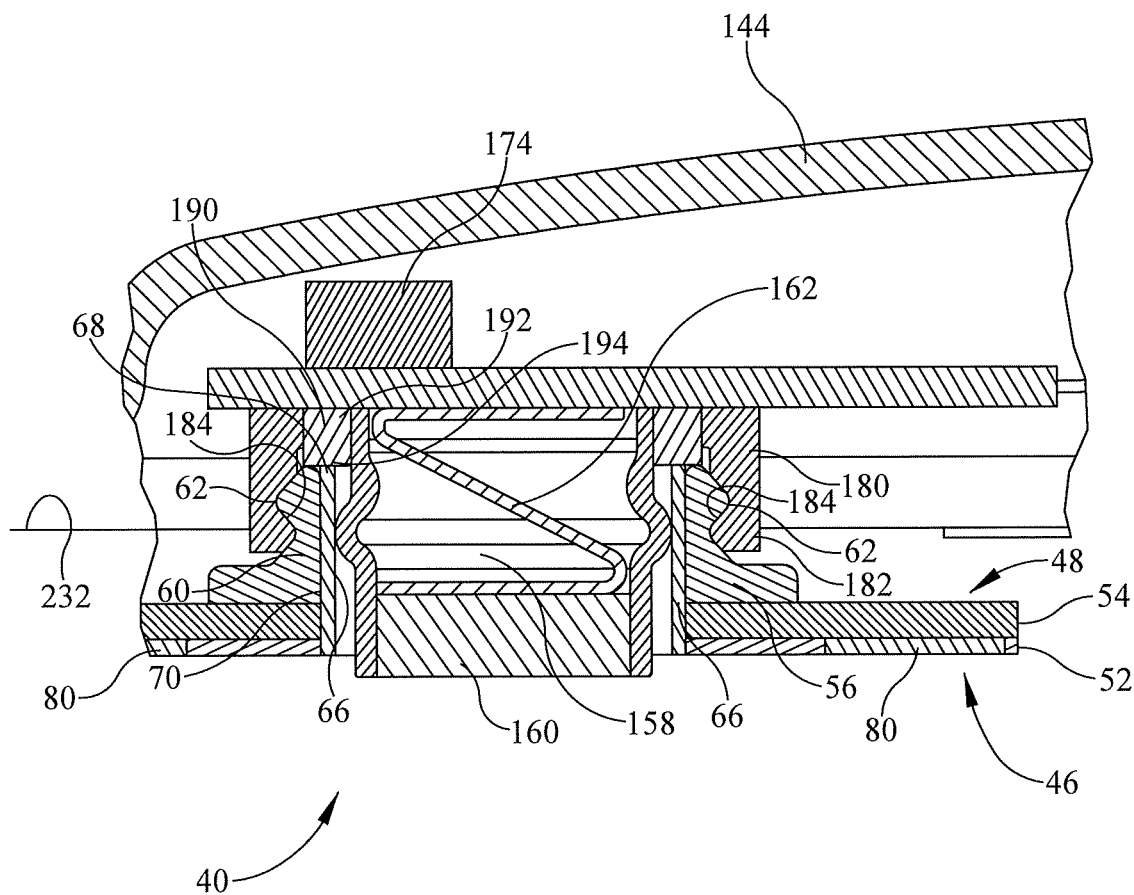
FIG. 3 is an enlarged view of a portion of FIG. 1 showing a cleat connector and a housing connector mated to each other and also showing an electrical connection between the cleat and the housing, a sensor cavity defined by the cleat connector and housing connector, and a sensor residing in the cavity.

Referring additionally to FIG. 3, the monitor includes a pair of cleats 40. Each cleat has a lower or patient facing side 46 and an upper or environment facing side 48. Each cleat includes an adhesive layer 52 for adhering the cleat to a patient's skin and a nonwoven tape layer 54. A peel-off protective liner 58 (shown only in FIG. 2) covers the lower side of the adhesive layer. A caregiver peels away the liner prior to adhering the cleat to a patient. Each cleat also includes a cleat connector 56. The illustrated cleat connector is an electrically nonconductive ring having a racetrack shaped planform. Wall 60 of the ring includes a perimetrical barb 62 and circumscribes a pair of cleat conductive members 66 each of which extends in the transverse direction along wall 60. Each cleat conductive member has an upper end 68 and a lower end 70.

One or both cleats includes at least one electrode 80 which is exposed on the patient facing side of the cleat. When the cleat is adhered to a patient's skin by way of adhesive layer 52, the exposed electrode contacts the patient's skin. A cleat electrical trace 82 extends laterally from each electrode along the environment facing side of the cleat and contacts the lower end 70 of cleat conductive member 66.

In the illustrated embodiment the electrodes are hydrogel electrocardiogram (ECG) electrodes, two of which are components of the headward cleat and two of which are components of the footward cleat. Only two electrodes are visible because the cleats are out of the plane of FIG. 1 and only the headward cleat is illustrated in FIG. 2.

The cleats are "subject wearable" in that they can be applied to a subject's skin by way of adhesive layer 52, will resist unintentional dislodgement over a specified interval of time (e.g. five days) under conditions of normal use, but can be readily removed from the subject whenever required. The phrase "conditions of normal use" refers to the conditions that the cleat is likely to encounter when adhered to a patient, and includes patient activity such as bathing, showering, and exposure to radiological procedures.

The monitor also includes an equipment module 100 having a lower or patient facing side 102 and an upper or environment facing side 104. Module 100 includes a housing 110 comprised of a base 112 and a dome or cover 114 adhesively held to each other at a seam 116. The base and cover define an equipment compartment 120. The housing is made of a material, such as a foam, which can be easily flexed by an applied force or moment but which is otherwise able to hold its own shape.

A circuit assembly 140 resides inside the equipment compartment. In the illustrated embodiment the circuit assembly is a printed circuit assembly (PCA). The circuit assembly comprises first (headward), second (footward), and third (middle) rigid segments 144, 146, 148. Electrically conductive intersegment connectors 154, connect the middle segment to the headward and footward segments. The illustrated intersegment connectors are flexible or are otherwise able to permit some spatial displacement of the segments relative to each other and relative to the housing. This capability of the intersegment connectors 154, and the flexibility of housing 110 enable the monitor to be attached even to curved portions of the patient's body and to remain attached even if the patient moves or flexes the muscles in the vicinity of the monitor.

The PCA (also referred to as a PCBA) is a printed circuit board (PCB) populated by electrical components (also referred to herein as electronic components). The electronic components are interconnected by PCA traces (not illustrated) on the PCB. The electronic components include at least a processor 166 for processing data signals which originate at electrodes 80 and at sensors 160 which are described in more detail below. The PCA may also include one or more amplifiers 168 and one or more filters 170 to amplify and de-noise the sensor and electrode signals. A transceiver 172 provides communication with remote devices such as information displays and user controls. In the illustration the electronic components are shown at arbitrary locations on the middle segment of the PCB.

Housing base 112 includes a housing connector 180. The housing connector is a ring having a wall 182 with a perimetrical notch 184. Wall 182 circumscribes a pair of housing electrical conductive members 190 each of which has an upper end 192 and a lower end 194. The upper end 192 of each housing conductive member contacts a PCA trace. As already noted the PCA traces are not illustrated.

The cleat connector 56 and housing connector 180 mate with or otherwise engage with each other to form a mechanical connection between the cleat and the equipment housing. In the illustrated monitor, barb 62 of the cleat connecter 56 mates with notch 184 of housing connector 180. When so connected, connector rings 56, 180 define a sensor cavity 158. In the illustrated embodiment a sensor 160 resides in the sensor cavity. Example sensors include photoplethysmogram (PPG) sensors, phonocardiogram (PCG) sensors, and oxygen saturation (SpO2) sensors. Alternatively the sensor cavity may be unoccupied. A sensor conductor member 162 provides electrical connection between the sensor and the PCA traces.

An ON/OFF switch 174 resides inside equipment compartment 120. The switch controls electrical communication between a battery assembly 210, which is described in more detail below, and circuit assembly 140. In the illustrated embodiment the switch is a push button located at the headward end of the compartment so that a user can operate it by pressing down on the overlying portion of flexible cover 112 without damaging the cover.

When the monitor is shipped by its manufacturer and received by the caregiver the equipment housing 110 is already mated to the cleats as seen in FIG. 1. A caregiver peels liner 58 off the adhesive 52 of each cleat and applies the cleats to the patient. The caregiver presses switch 174 to power the electronic components and begin monitoring of the patient's vital signs.

The cleats are resistant to damage by water and medical radiation. The equipment housing and its electronic components are not. Therefore, before the patient bathes or showers or undergoes a radiological procedure, the caregiver first detaches the housing from the cleats, leaving the cleats in place on the patient's skin. Later, when it is desired to re-attach the housing to the cleats, the caregiver aligns the housing with the cleats so that each housing connector 180 registers with a cleat connector 56. The caregiver then presses connector elements 56, 180 against each other causing the walls 60, 182 of the connectors to deflect so that barb 62 re-engages notch 184 to make a mechanical connection between the cleat and the equipment housing. The housing may be repeatedly disconnected from the cleats and reconnected to the cleats. Accordingly, housing 110 is removably attached to (and detachable from) cleats 40. "Removably attached" means that the housing can be detached or disconnected from the cleats (and attached or connected to the cleats) without the use of tools or equipment and with the exertion of only a modest force. "Removably attached" additionally means that the housing can be repeatedly attached to and detached from the cleats.

In addition to the above described mechanical connection, when the cleat connector 56 and housing connector 180 are in a mating relationship with each other, the upper end 68 of each cleat conductive member 66 mates with or otherwise engages the lower end 194 of its counterpart housing conductive member 190. In addition, sensor conductive member 162 connects sensor 160 to circuit assembly 140. As a result the illustrated connectors 56, 180 are combination mechanical/electrical connectors providing a combination of both a mechanical connection between the cleat and the housing and an electrical connection between the electrical components of the cleat and the electrical components of the housing. Signals detected by electrodes 80 reach their destination components on the PCA by way of a path defined by cleat traces 82, cleat conductive members 66, housing conductive members 190 and the un-illustrated PCA traces. Signals detected detected by sensor 160 reach their destination components on the PCA by way of a path defined by sensor conductor member 162 and the un-illustrated PCA traces.

In other embodiments, the above described commonality of the mechanical and electrical connections may be absent. Nevertheless, the cleat mechanical connector and the housing mechanical connector would be engageable with each other to define a mechanical connection between the cleat and the equipment housing and would also be disengageable from each other. Similarly, the cleat conductive member and the housing conductive member would be engageable with each other to define an electrical connection between the cleat and the equipment housing, and would also be disconnectable from each other to break that electrical connection.

Figure 8:
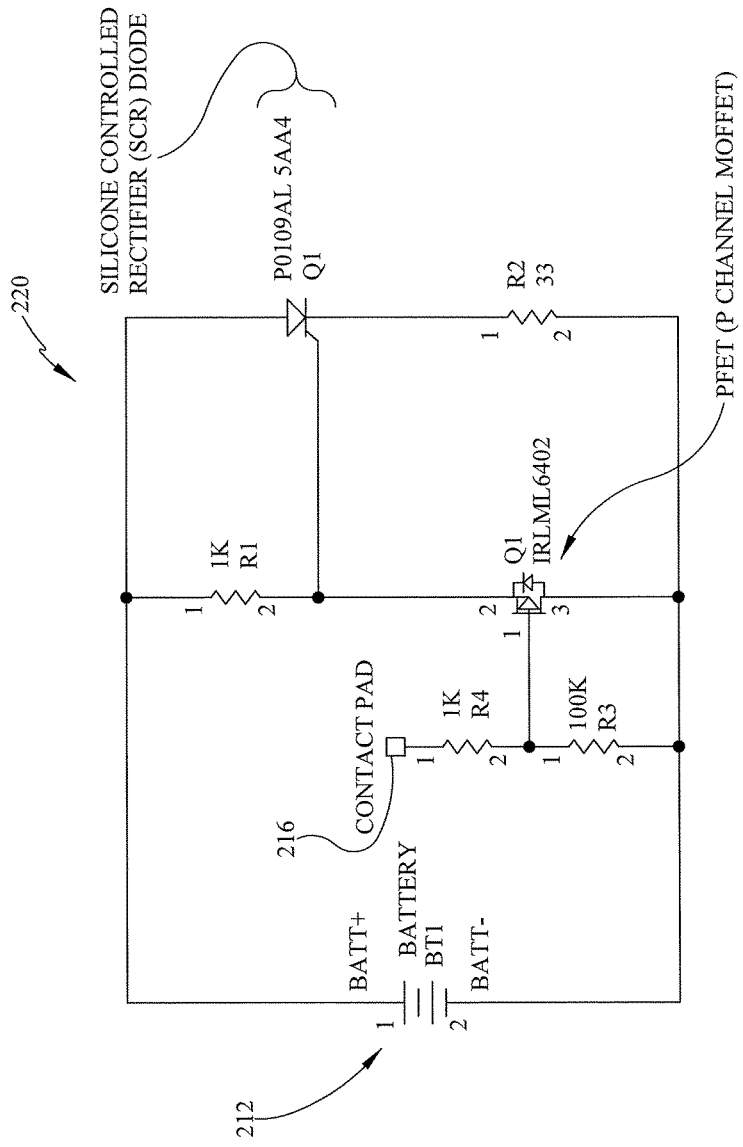
FIG. 8 is a schematic view of a battery discharge circuit for the vital signs monitor.

The monitor also includes a battery assembly 210 comprised of a battery 212 and a patch circuit assembly 214 having gold plated pads 216 on its upper surface. Three of the pads correspond to terminals of battery 212 (two positive and one negative or vice versa). One of the pads is connected to a battery discharge circuit 220 shown schematically in FIG. 8 in the context of one of the pads 216. Electrically conductive contact springs 224 extend from each pad 216 to the middle segment 148 of circuit assembly 140, forming a connection between the battery assembly and the circuit assembly in order to transfer electrical energy from the battery to the components of circuit assembly.

Battery assembly 210 is housed within a battery subcompartment 226 of the equipment compartment 120. The illustrated battery compartment is defined in part by a battery housing 228. Middle segment 148 of the circuit assembly rests atop the battery housing and is therefore transversely offset from headward and footward segments 144, 146. The transverse offset of middle segment 148 from a bottom plane 232 of the housing exceeds the transverse offset of the headward and footward segments 144, 146 from the bottom plane. The battery compartment extends transversely from middle circuit assembly segment 148 to a battery retainer 230. Therefore the battery assembly resides transversely between segment 148 and the bottom plane 232 and does not project transversely outwardly beyond the bottom plane. As a result the monitor can more easily conform to the shape of the patient's body.

Figure 4:
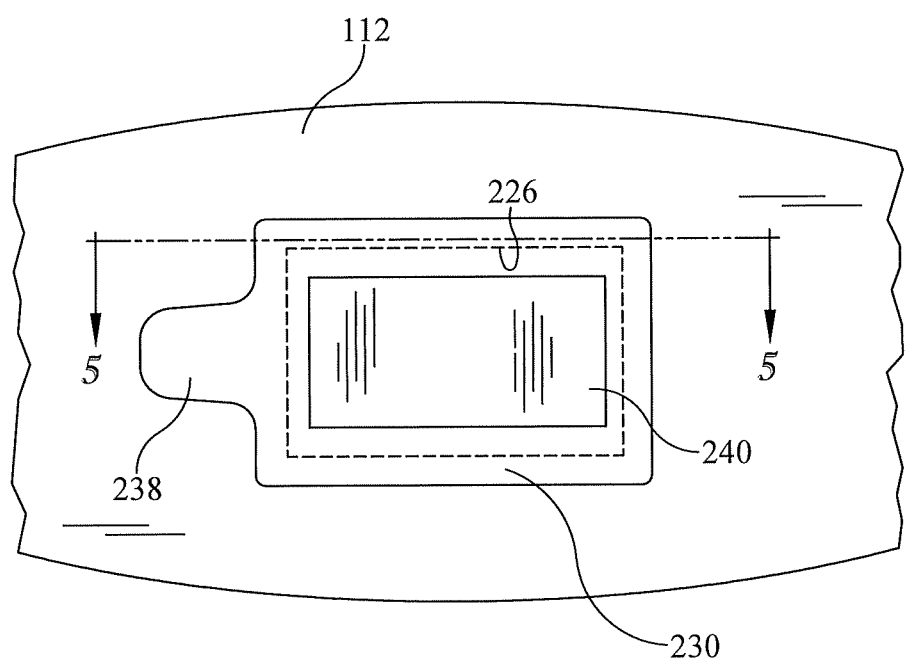
FIG. 4 is a plan view of the patient facing side of the equipment housing showing a battery retainer covering a battery compartment of the housing.
Figure 5:
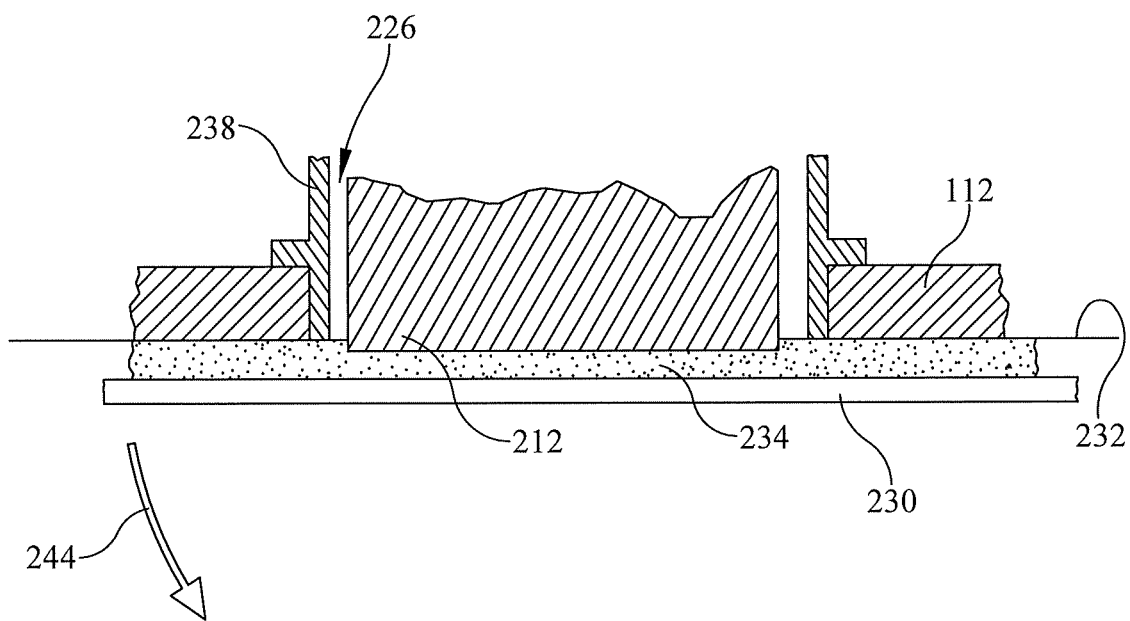
FIG. 5 is a view in the direction 5-5 of FIG. 4 enlarged to show an adhesive securing the retainer to the base of the equipment housing and to a battery.

Referring additionally to FIGS. 4-5, battery retainer 230 is a thin sheet of material joined to the patient facing side of the equipment housing along its bottom plane 232, for example by an adhesive 234, in order to retain the battery assembly inside the housing. In FIG. 5, the thicknesses of the retainer and adhesive are exaggerated for illustrative clarity. In the embodiment of FIG. 5 the adhesive also adheres the retainer to the battery. The adhesive holding the retainer to the battery need not be the same as the adhesive holding the retainer to the housing base 112. Moreover, the adhesive between the retainer and the battery may be omitted. As seen best in FIG. 4, the lateral and longitudinal dimensions of the retainer are larger than those of battery compartment 226. The retainer includes a tab 238 and may have instructions 240 printed thereon.

Figure 6:
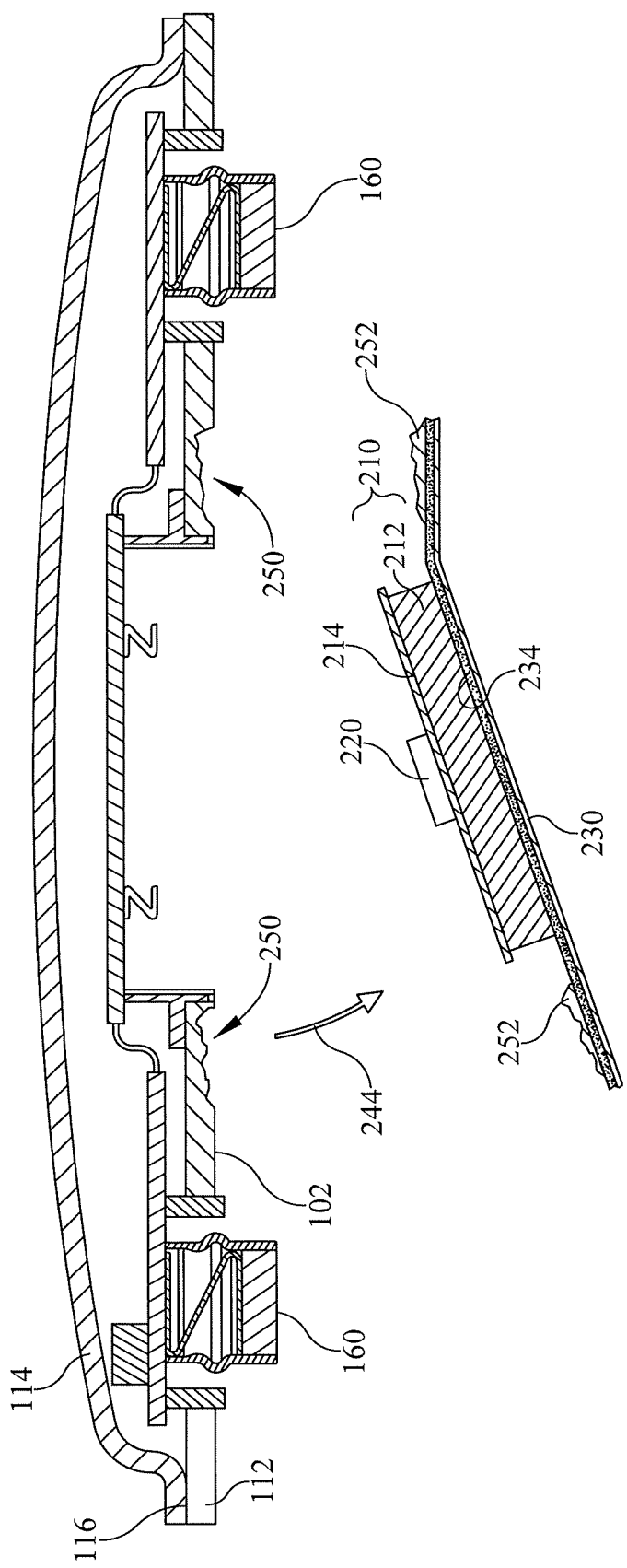
FIG. 6 is a cross sectioned elevation view of the vital signs monitor showing the retainer pulled away from the equipment module in order to remove the battery assembly.

Referring to FIG. 6, retainer 230 is separable from the housing. In practice a caregiver first disconnects the housing from the cleats and then pulls on retainer tab 238 in a direction indicated by arrow 244 of FIGS. 1, 5 and 6, thereby peeling the retainer off the base 112 of the equipment housing and separating the retainer from the housing. Separation of the retainer breaks the connection between battery assembly 210 and circuit assembly 140 and activates discharge circuit 220 which drains any residual charge from the battery. Separation of the retainer also damages the housing as indicated by the torn regions 250 of the housing base and the corresponding remnants 252 of the housing material sticking to the retainer. The torn regions 250 provide a visual indication that a replacement battery, even if available, should not be installed in the housing. If a caregiver nevertheless acquires a replacement battery and attempts to install it, the retainer is unlikely to adhere properly to the damaged housing base, further alerting the caregiver that the battery should not be replaced.

Provided the battery assembly is adhered to the retainer, separation of the retainer from the equipment housing withdraws the battery assembly from the equipment compartment. In a configuration in which there is no adhesive 234 between the battery assembly and the retainer, and assuming the patient facing side 102 of the housing faces downwardly, separation of the retainer may also cause the battery to be withdrawn from the housing in the sense that gravity will cause the battery to drop out of the compartment. If the caregiver holds the housing so that its patient facing side faces upwardly, separation of the retainer will render the unadhered battery removable because the caregiver merely needs to lift the battery out of its compartment in order to remove the battery from the monitor.

Figure 7:
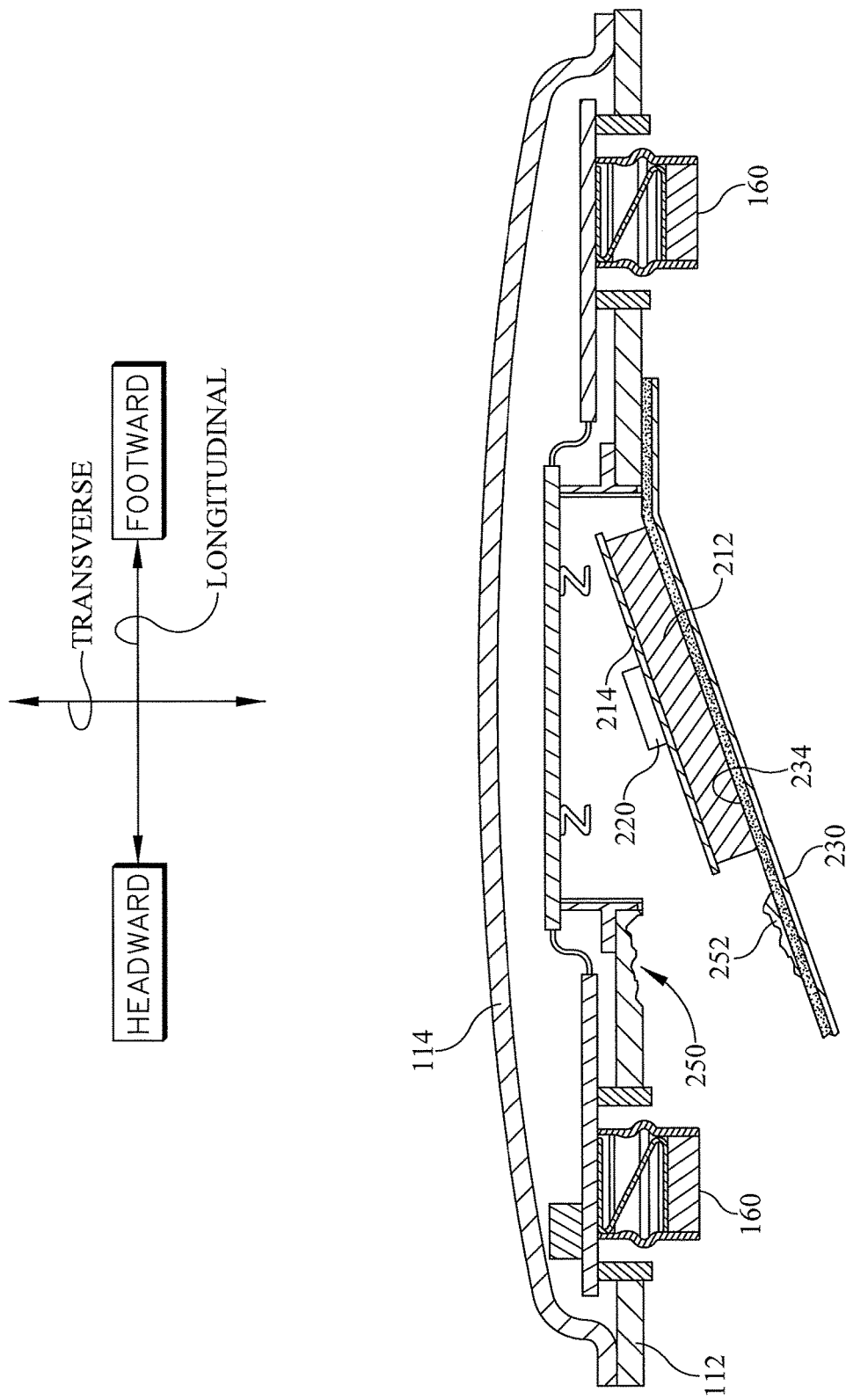
FIG. 7 is a cross sectioned elevation view of the vital signs monitor showing the retainer partially pulled away from the equipment module in order to remove the battery assembly.

As used herein, separation of the retainer refers to complete separation of the retainer from the equipment housing as seen in FIG. 6, and also to partial separation. FIG. 7 shows an example in which the retainer has been only partially separated from the equipment housing. The footward end of the battery assembly still projects into the battery subcompartment 226 and therefore the battery assembly might be viewed as not having been completely withdrawn from equipment compartment 120. Nevertheless the electrical connection between battery assembly 210 and circuit assembly 140, has been interrupted, the housing has been damaged (as indicated by torn regions 250 and remnants 252) and the discharge circuit 214 has been activated to drain any residual charge from the battery, just as in FIG. 6. The partial separation of the retainer has effectively withdrawn the battery from equipment compartment 120 or has rendered the battery removable from the monitor. Battery removability can be facilitated by selecting an adhesive 234 whose bond to the battery assembly is weak enough that a user can easily separate the battery assembly from the retainer. If no adhesive is present between the battery assembly and the retainer, the battery will drop out under the influence of gravity or can be lifted out by the caregiver as described above in connection with FIG. 6.

From time to time ON/OFF switch 174 may be used to interrupt electrical communication between the battery assembly 210 and the circuit assembly 140. For example the switch may be used to power down the circuit assembly when the equipment housing is disconnected from the cleats in order to accommodate patient bathing or showering or in preparation for carrying out a radiological procedure. The discharge circuit is adapted to not discharge the battery in response to use of the ON/OFF switch.

Although this disclosure refers to specific embodiments, it will be understood by those skilled in the art that various changes in form and detail may be made without departing from the subject matter set forth in the accompanying claims.

The invention claimed is:
1. A vital signs monitor comprising:
   an equipment housing including a base and a flexible cover, the base and the flexible cover defining an equipment compartment, a bottom plane of the base defining a patient-facing side of the base;
   a circuit assembly residing inside the equipment compartment;

a battery assembly residing, at least in part, in the equipment compartment, a portion of the circuit assembly overlaying the battery assembly such that the battery assembly is disposed transversely between the portion of the circuit assembly and the bottom plane of the base;

a switch residing inside the equipment compartment, the switch selectively controlling an electrical connection between the battery assembly and the circuit assembly, the switch being operable via the flexible cover;

a discharge circuit; and a retainer joined to the patient-facing side of the base thereby retaining the battery assembly, at least in part, in the equipment compartment, the retainer being separable from the patient-facing side of the base so that separation of the retainer from the housing causes a break in the electrical connection and activates the discharge circuit, the discharge circuit being configured to discharge a battery of the battery assembly carried by the retainer after the circuit assembly has been powered down via operation of the switch.

2. The monitor of claim 1 wherein separation of the retainer also removes the battery from the monitor or renders it removable.

3. The monitor of claim 1 wherein the retainer is joined to the battery assembly and wherein separation of the retainer from the housing withdraws the battery assembly from the equipment compartment.

4. The monitor of claim 1 wherein the base further includes an upper side opposite the patient-facing side, the upper side of the base mating with the flexible cover and defining part of the equipment compartment.

5. The monitor of claim 1 wherein the patient-facing side of the base is spaced from a skin surface of a patient when the monitor is worn by the patient on the skin surface.

6. The monitor of claim 1 wherein the circuit assembly comprises a first circuit assembly, the monitor further comprising a second circuit assembly carried by the retainer,
 a first component of the second circuit assembly being electrically connected to the discharge circuit, and
 a second component of the second circuit assembly being electrically connected to the battery and the first circuit assembly.

7. The monitor of claim 6, wherein separating the retainer from the housing causes at least part of the housing to be removed with the retainer, and wherein the second circuit assembly is disposed between the battery and the portion of the first circuit assembly.

8. The monitor of claim 1 wherein the circuit assembly is a segmented assembly, a first segment of which is transversely offset from the bottom plane by a second segment of the circuit assembly and by a third segment of the circuit assembly, and wherein the battery assembly resides transversely between the more offset segment and the bottom plane,
 the first segment being movably connected to the second segment by a first electrically conductive connector, and being movably connected to the third segment by a second electrically conductive connector, the first and second electrically conductive connectors permitting movement of the first segment relative to the housing.

9. The monitor of claim 1 including one or more cleats.

10. The monitor of claim 9 wherein at least one of the cleats includes a cleat connector, the equipment housing includes a housing connector, the cleat and housing connectors being engageable with each other to define a mechanical connection between the cleat and the equipment housing and also being disconnectable from each other.

11. The monitor of claim 9 wherein at least one of the cleats includes an electrode and a cleat conductive member, the equipment housing includes a housing conductive member, the cleat conductive member and the housing conductive member being engageable with each other to define an electrical connection between the cleat and the equipment housing and also being disconnectable from each other to break the electrical connection between the cleat and the equipment housing.

12. The monitor of claim 9 wherein at least one of the cleats includes an electrode and a cleat combination connector, the equipment housing includes a housing combination connector, the cleat and housing combination connectors being connectable to each other to define a combined mechanical and electrical connection between the cleat and the equipment housing and also being disconnectable from each other to break the combined mechanical and electrical connection between the cleat and the equipment housing.

13. The monitor of claim 1, wherein activation of the discharge circuit causes discharge of the battery after the battery has been removed from the housing.

14. The monitor of claim 1, wherein separation of the retainer from the housing removes the discharge circuit from the housing.

15. The monitor of claim 1, wherein a component of the discharge circuit is carried by the retainer.

16. The monitor of claim 1, wherein the base of the housing includes a connector configured to mate with an equipment housing, the equipment housing being configured to be adhered to a skin surface of a patient.

17. The monitor of claim 16, wherein the connector comprises a ring-shaped wall having a pair of conductive members, the pair of conductive members being operably connected to the circuit assembly.

18. The monitor of claim 17, wherein the ring-shaped wall forms at least part of a sensor cavity, a sensor of the equipment housing being disposed at least partly within the sensor cavity when the connector is mated with the equipment housing.

19. A vital signs monitor comprising:
 an equipment housing including a base and a flexible cover, the base and the flexible cover defining an equipment compartment, a bottom plane of the base defining a patient-facing side of the base;
 a circuit assembly residing inside the equipment compartment, the circuit assembly including at least one electrical component;
 a battery assembly residing, at least in part, in the equipment compartment, a portion of the circuit assembly overlaying the battery assembly such that the battery assembly is disposed transversely between the portion of the circuit assembly and the bottom plane of the base;
 a switch residing inside the equipment compartment, the switch selectively controlling electrical communication between the battery assembly and the circuit assembly, the switch being operable via the flexible cover;
 a discharge circuit adapted to:
   not discharge a battery carried by the battery assembly in response to interruption of the electrical communication between the battery assembly and the circuit assembly by way of the switch, discharge the battery in response to interruption of the electrical communication between the battery assembly and the circuit assembly by an action other than use of the switch, and discharge the battery after the circuit assembly has been powered down via operation of the switch; and a retainer joined to the patient-facing side of the base thereby retaining the battery assembly, at least in part, in the equipment compartment, the retainer being separable from the patient-facing side of the base to remove the battery assembly from the equipment compartment.

20. The monitor of claim 19
wherein the action other than use of the switch is separation of the retainer from the equipment housing.

* * * * *